(12) United States Patent
Wu et al.

(10) Patent No.: US 10,660,731 B2
(45) Date of Patent: May 26, 2020

(54) INTRAORAL SCANNING SYSTEM AND INTRAORAL SCANNING METHOD

(71) Applicant: QISDA CORPORATION, Taoyuan (TW)

(72) Inventors: Chuang-Wei Wu, Taipei (TW); Yen-Tsun Lin, Taichung (TW); Po-Fu Wu, New Taipei (TW)

(73) Assignee: Qisda Corporation, Taoyuan (TW)

( * ) Notice: Subject to any disclaimer, the term of this patent is extended or adjusted under 35 U.S.C. 154(b) by 93 days.

(21) Appl. No.: 16/115,527

(22) Filed: Aug. 28, 2018

(65) Prior Publication Data

US 2020/0054420 A1    Feb. 20, 2020

(30) Foreign Application Priority Data

Aug. 15, 2018 (CN) .......................... 2018 1 0931025

(51) Int. Cl.
| | |
|---|---|
| *A61C 9/00* | (2006.01) |
| *G06T 1/00* | (2006.01) |
| *G16H 30/40* | (2018.01) |
| *G06T 7/20* | (2017.01) |
| *G06T 17/00* | (2006.01) |

(52) U.S. Cl.
CPC .......... *A61C 9/0053* (2013.01); *G06T 1/0007* (2013.01); *G06T 7/20* (2013.01); *G16H 30/40* (2018.01); *G06T 17/00* (2013.01); *G06T 2200/08* (2013.01)

(58) Field of Classification Search
CPC ....... A61C 9/0053; G06T 1/0007; G06T 7/20; G06T 2200/08; G06T 17/00; G16H 30/40
See application file for complete search history.

(56) References Cited

U.S. PATENT DOCUMENTS

| | | | | |
|---|---|---|---|---|
| 2015/0320320 | A1* | 11/2015 | Kopelman | ........... A61B 5/4547 433/24 |
| 2016/0163115 | A1* | 6/2016 | Furst | .................... A61B 8/5261 433/29 |
| 2016/0217708 | A1* | 7/2016 | Levin | .................... G06F 3/0481 |
| 2018/0028065 | A1* | 2/2018 | Elbaz | ........................ G06T 7/55 |

* cited by examiner

*Primary Examiner* — Neil R McLean

(57) ABSTRACT

An intraoral scanning system includes a motion sensing unit, an image sensing unit, a storage unit and a processing unit. The processing unit classifies first position information and second position information obtained by the motion sensing unit and the image sensing unit in an initial scanning process into first groups and second groups, wherein the first position information and the second position information are stored in the storage unit. The processing unit selectively uses the first groups or the second groups to perform comparison in a re-scanning process, so as to position an incomplete area in a model.

14 Claims, 6 Drawing Sheets

INTRAORAL SCANNING SYSTEM AND INTRAORAL SCANNING METHOD

BACKGROUND OF THE INVENTION

1. Field of the Invention

The invention relates to an intraoral scanning system and an intraoral scanning method and, more particularly, to an intraoral scanning system and an intraoral scanning method capable of reducing the amount of data for comparison in a re-scanning process effectively.

2. Description of the Prior Art

An intraoral scanner uses laser to scan tooth rapidly and then transmits the scanned image to a computer, so as to establish a tooth model. In general, due to limitations of structure or operation, the tooth model cannot be established completely through one single scanning process. Accordingly, an operator has to use the intraoral scanner to perform a re-scanning process for tooth, so as to re-model an incomplete area (e.g. broken area) in the tooth model. The amount of data obtained in the re-scanning process is huge. If the huge amount of data is compared with the tooth model established previously one by one, lots of computation resources and time will be consumed, such that the tooth model cannot be established efficiently.

SUMMARY OF THE INVENTION

An objective of the invention is to provide an intraoral scanning system and an intraoral scanning method capable of reducing the amount of data for comparison in a re-scanning process effectively, so as to solve the aforesaid problems.

According to an embodiment of the invention, an intraoral scanning system comprises a motion sensing unit, an image sensing unit, a storage unit and a processing unit. The motion sensing unit senses a plurality of first initial position information in an initial scanning process of the intraoral scanning system. The image sensing unit captures a plurality of initial images for an object in the initial scanning process. The processing unit is coupled to the motion sensing unit, the image sensing unit and the storage unit. The processing unit converts the initial images into a plurality of second initial position information and stores the first position information and the second initial position information in the storage unit. The processing unit establishes a model of the object according to the second initial position information, classifies the first initial position information into a plurality of first groups, and classifies the second initial position information into a plurality of second groups. When an incomplete area exists in the model, the intraoral scanning system performs a re-scanning process for the object. The motion sensing unit senses at least one first current position information in the re-scanning process. The image sensing unit captures at least one current image for the object in the re-scanning process. The processing unit converts the at least one current image into at least one second current position information. The processing unit selectively compares the first groups with the at least one first current position information or compares the second groups with the at least one second current position information, so as to position the incomplete area in the model.

According to another embodiment of the invention, an intraoral scanning method comprises steps of sensing a plurality of first initial position information in an initial scanning process by a motion sensing unit; capturing a plurality of initial images for an object in the initial scanning process by an image sensing unit; converting the initial images into a plurality of second initial position information; establishing a model of the object according to the second initial position information; classifying the first initial position information into a plurality of first groups and classifying the second initial position information into a plurality of second groups; when an incomplete area exists in the model, performing a re-scanning process for the object; sensing at least one first current position information in the re-scanning process by the motion sensing unit; capturing at least one current image for the object in the re-scanning process by the image sensing unit; converting the at least one current image into at least one second current position information; and selectively comparing the first groups with the at least one first current position information or comparing the second groups with the at least one second current position information, so as to position the incomplete area in the model.

As mentioned in the above, the invention classifies the first position information and the second position information obtained by the motion sensing unit and the image sensing unit in the initial scanning process into first groups and second groups. Then, the invention selectively uses the first groups or the second groups to perform comparison in the re-scanning process, so as to position the incomplete area in the model. Since the invention need not compare all position information obtained in the re-scanning process with the model established previously one by one, the invention can reduce the amount of data for comparison in the re-scanning process effectively, so as to save computation resources and time.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
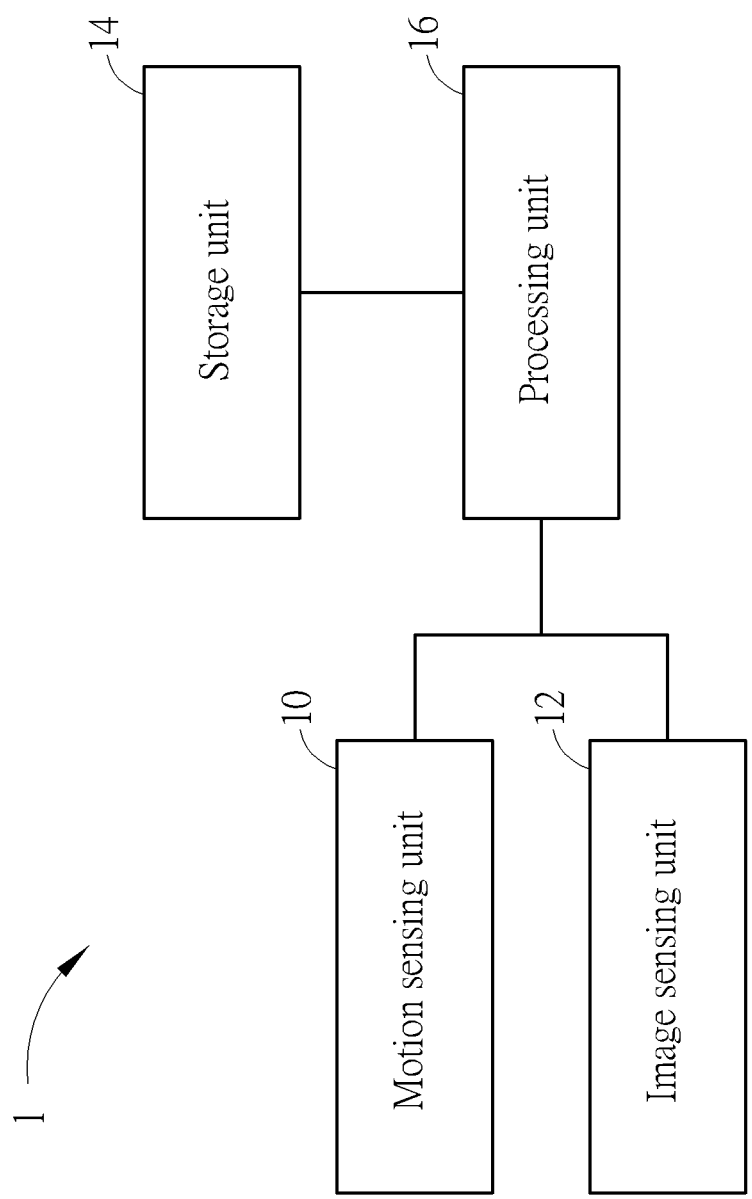
FIG. 1 is a functional block diagram illustrating an intraoral scanning system according to an embodiment of the invention.

Referring to FIG. 1, FIG. 1 is a functional block diagram illustrating an intraoral scanning system 1 according to an embodiment of the invention. As shown in FIG. 1, the intraoral scanning system 1 comprises a motion sensing unit 10, an image sensing unit 12, a storage unit 14 and a processing unit 16, wherein the processing unit 16 is coupled to the motion sensing unit 10, the image sensing unit 12 and the storage unit 14. In this embodiment, the motion sensing unit 10, the image sensing unit 12, the storage unit 14 and the processing unit 16 may be disposed in an intraoral scanner, so as to constitute the intraoral scanning system 1 of the invention. In another embodiment, the motion sensing unit 10 and the image sensing unit 12 may be disposed in an intraoral scanner and the storage unit 14 and the processing unit 16 may be disposed in a host device, so as to constitute the intraoral scanning system 1 of the invention. In other words, the intraoral scanning system 1 of the invention may be an intraoral scanner or a combination of intraoral scanner and host device.

In practical applications, the motion sensing unit 10 may be a G sensor, a gyro or a combination thereof; the image sensing unit 12 may be a charge-coupled device (CCD) sensor, a complementary metal-oxide semiconductor (CMOS) sensor or other sensors, the storage unit 14 may be a memory or other data storage devices; the processing unit 16 may be a processor or a controller with data calculating/processing function. In general, the aforesaid intraoral scanner may be further equipped with some necessary hardware or software components for specific purposes, such as a circuit board, applications, a communication module, a digital light processing (DLP) module, a power supply, etc., the aforesaid host device may be further equipped with some necessary hardware or software components for specific purposes, such as a circuit board, applications, a communication module, a power supply, etc., and it depends on practical applications.

Figure 2:
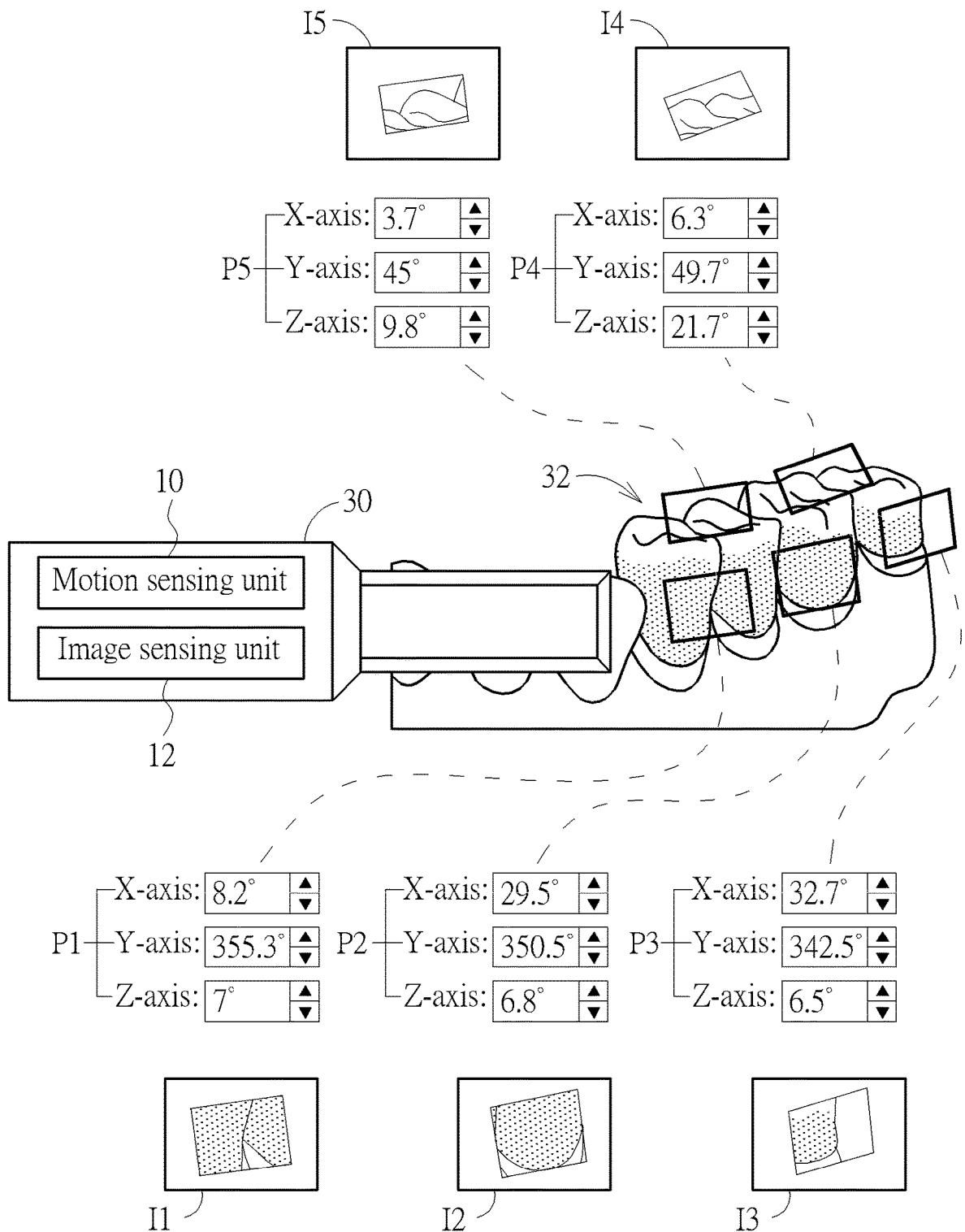
FIG. 2 is a schematic diagram illustrating that an intraoral scanner is scanning an object.
Figure 3:
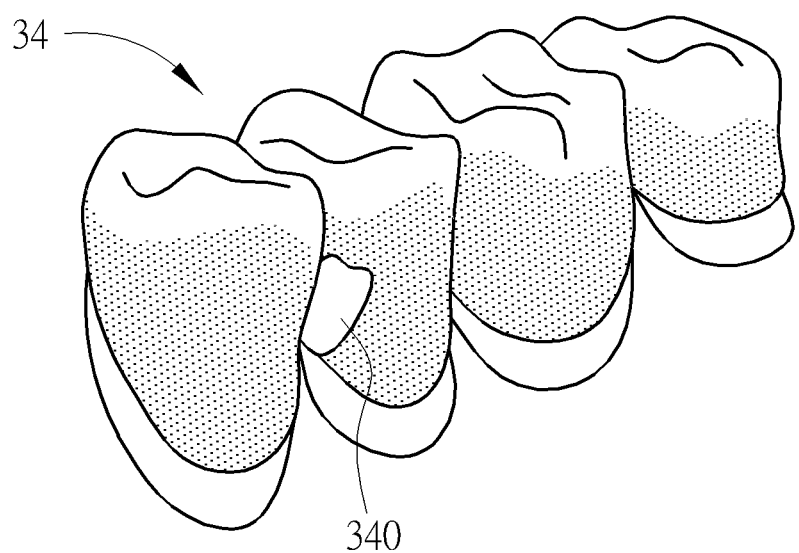
FIG. 3 is a schematic diagram illustrating a model established according to the object shown in FIG. 2.

Referring to FIGS. 2 and 3, FIG. 2 is a schematic diagram illustrating that an intraoral scanner 30 is scanning an object 32 and FIG. 3 is a schematic diagram illustrating a model 34 established according to the object 32 shown in FIG. 2. As shown in FIG. 2, first, a user may operate the intraoral scanner 30 to perform an initial scanning process for the object 32, wherein the aforesaid motion sensing unit 10 and image sensing unit 12 are disposed in the intraoral scanner 30. At this time, the motion sensing unit 10 senses a plurality of first initial position information P1-P5 in the initial scanning process and the image sensing unit 12 captures a plurality of initial images I1-I5 for the object 32 in the initial scanning process. In this embodiment, the object 32 is tooth. Furthermore, each of the first initial position information P1-P5 may be represented by angle information including X-axis, Y-axis and Z-axis. After the motion sensing unit 10 senses the plurality of first initial position information P1-P5, the processing unit stores the first initial position information P1-P5 in the storage unit 14.

After capturing the initial images I1-I5, the processing unit 16 converts the initial images I1-I5 into a plurality of second initial position information and stores the second initial position information in the storage unit 14. In this embodiment, each of the second initial position information may be represented by angle information including X-axis, Y-axis and Z-axis. Then, the processing unit 16 establishes a model 34 of the object 32 according to the second initial position information, as shown in FIG. 3.

Then, the processing unit classifies the first initial position information into a plurality of first groups and classifies the second initial position information into a plurality of second groups. In this embodiment, the processing unit 16 may classify the first initial position information into the first groups and classify the second initial position information into the second groups according to a predetermined angle range (e.g. 15 degrees, 30 degrees, and so on).

Figure 4:
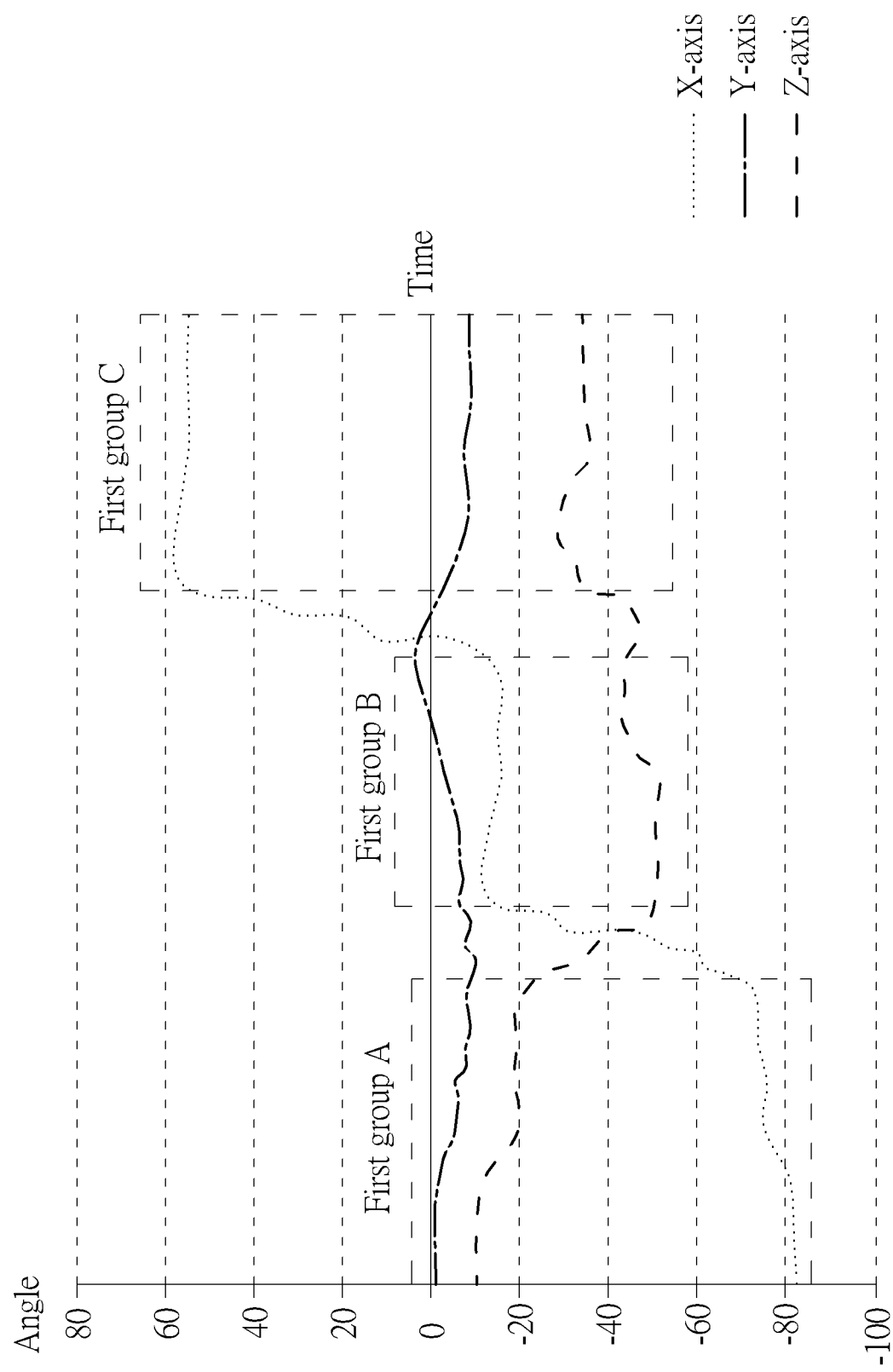
FIG. 4 is a graph illustrating that the angle information of X-axis, Y-axis and Z-axis of the first initial position information varies with time.

Referring to FIG. 4, FIG. 4 is a graph illustrating that the angle information of X-axis, Y-axis and Z-axis of the first initial position information varies with time. When the variations of the angle information of X-axis, Y-axis and Z-axis of the first initial position information all are smaller than the predetermined angle range within a continuous span of time, it means that the intraoral scanner is situated in a stable scanning state. At this time, the processing unit 16 may classify the angle information of X-axis, Y-axis and Z-axis of the first initial position information within the continuous span of time into an identical group. When the variation of the angle information of any axis is larger than the predetermined angle range, it means that the motion of the intraoral scanner is violent, i.e. the intraoral scanner is situated in an unstable scanning state. At this time, the processing unit 16 may not classify the angle information with larger variation. Accordingly, as shown in FIG. 4, the processing unit 16 may classify the curves into three groups A, B, C. The manner of classifying the second initial position information is identical to the manner of classifying the first initial position information, so it will not be depicted herein again.

As shown in FIG. 3, when an incomplete area 340 (e.g. broken area) exists in the model 34, the user may operate the intraoral scanner 30 to perform a re-scanning process for the object 32. At this time, the motion sensing unit 10 senses at least one first current position information in the re-scanning process and the image sensing unit 12 captures at least one current image for the object 32 in the re-scanning process. After capturing the at least one current image, the processing unit 16 converts the at least one current image into at least one second current position information. In this embodiment, the first current position information and the second current position information may be represented by angle information including X-axis, Y-axis and Z-axis.

Then, the processing unit 16 may selectively compare the first groups with the at least one first current position information or compare the second groups with the at least one second current position information, so as to position the incomplete area 340 in the model 34. In this embodiment, the processing unit 16 may selectively compare the first groups with the at least one first current position information or compare the second groups with the at least one second current position information according to an image quality of the current image, wherein the image quality may be represented by contrast ratio, acutance or amount of data points. In this embodiment, the data point may be voxel.

Taking the amount of data points for example, the invention may set an amount threshold. When the amount of data points is smaller than the amount threshold, it means that the image quality is bad. Accordingly, the processing unit 16 may compare the first groups obtained by the motion sensing unit 10 with the at least one first current position information, so as to position the incomplete area 340 in the model 34. On the other hand, when the amount of data points is larger than the amount threshold, it means that the image quality is good. Accordingly, the processing unit 16 may compare the second groups obtained by the image sensing unit 12 with the at least one second current position information, so as to position the incomplete area 340 in the model 34. Similarly, the invention may set a contrast threshold or an acutance threshold and then determine the image quality according to contrast ratio or acutance.

When the processing unit 16 compares the first groups with the at least one first current position information, the processing unit 16 selects a target first group, which is more approximate to the at least one first current position information, from the first groups and compares the target first group with the at least one first current position information, so as to position the incomplete area 340 in the model 34. On the other hand, when the processing unit 16 compares the second groups with the at least one second current position information, the processing unit 16 selects a target second group, which is more approximate to the at least one second current position information, from the second groups and compares the target second group with the at least one second current position information, so as to position the incomplete area 340 in the model 34.

Referring to Table 1 below, Table 1 classifies the first initial position information and the second initial position information into a plurality of first groups and a plurality of second groups for different areas Z1-Z3, respectively. It should be noted that the values shown in Table 1 is for illustration purpose only and the invention is not limited to the values shown in Table 1. Furthermore, X, Y and Z shown in Table 1 represent the angle information of X-axis, Y-axis and Z-axis of the first initial position information and the second initial position information. Table 1 further records the amount of data points corresponding to each of the areas Z1-Z3 for determining the image quality.

with the at least one second current position information, so as to position the incomplete area 340 in the model 34.

Provided that the aforesaid amount threshold is set to be 10000 and the incomplete area 340 is located in the area Z2. Since the amount of data points (3000) of the area Z2 is smaller than the amount threshold (10000), it means that the image quality of the area Z2 obtained in the re-scanning process is bad. Accordingly, the processing unit 16 may compare the first groups G1-Z2-1 to G1-Z2-n obtained by the motion sensing unit 10 with the at least one first current position information, so as to position the incomplete area 340 in the model 34. At this time, the processing unit 16 selects a target first group (e.g. G1-Z2-4), which is more approximate to the at least one first current position information, from the first groups G1-Z2-1 to G1-Z2-n and compares the target first group G1-Z2-4 with the at least one first current position information, so as to position the incomplete area 340 in the model 34.

After positioning the incomplete area 340 in the model 34, the processing unit 16 may re-model the incomplete area

TABLE 1

| Area | First initial position information (unit: degree) | | Second initial position information (unit: degree) | | Image quality (amount of data points) |
|---|---|---|---|---|---|
| Z1 | First group G1-Z1-1 | 0 < X < 30 0 < Y < 20 | Second group G2-Z1-1 | 5 < X < 30 2 < Y < 22 | 50000 |
| | First group G1-Z1-2 | 0 < Z < 10 | Second group G2-Z1-2 | 0 < Z < 10 | |
| | . . . First group G1-Z1-n | | . . . Second group G2-Z1-n | | |
| Z2 | First group G1-Z2-1 | 30 < X < 50 20 < Y < 30 | Second group G2-Z2-1 | 35 < X < 55 22 < Y < 32 | 3000 |
| | First group G1-Z2-2 | 3 < Z < 13 | Second group G2-Z2-2 | 3 < Z < 13 | |
| | . . . First group G1-Z2-n | | . . . Second group G2-Z2-n | | |
| Z3 | First group G1-Z3-1 | 30 < X < 50 30 < Y < 90 | Second group G2-Z3-1 | 35 < X < 55 32 < Y < 92 | 20000 |
| | First group G1-Z3-2 | 3 < Z < 13 | Second group G2-Z3-2 | 3 < Z < 13 | |
| | . . . First group G1-Z3-n | | . . . Second group G2-Z3-n | | |

As shown in Table 1, in the initial scanning process, the motion sensing unit 10 and the image sensing unit 12 may obtain the first initial position information and the second initial position information for different areas Z1-Z3 of the object 32. Then, the processing unit 16 classifies the first initial position information and the second initial position information into a plurality of first groups and a plurality of second groups for different area Z1-Z3.

Provided that the aforesaid amount threshold is set to be 10000 and the incomplete area 340 is located in the area Z1. Since the amount of data points (50000) of the area Z1 is larger than the amount threshold (10000), it means that the image quality of the area Z1 obtained in the re-scanning process is good. Accordingly, the processing unit 16 may compare the second groups G2-Z1-1 to G2-Z1-n obtained by the image sensing unit 12 with the at least one second current position information, so as to position the incomplete area 340 in the model 34. At this time, the processing unit 16 selects a target second group (e.g. G2-Z1-2), which is more approximate to the at least one second current position information, from the second groups G2-Z1-1 to G2-Z1-n and compares the target second group G2-Z1-2

340 accordingly. It should be noted that how to re-model is well known by one skilled in the art, so it will not be depicted herein.

Figure 5:
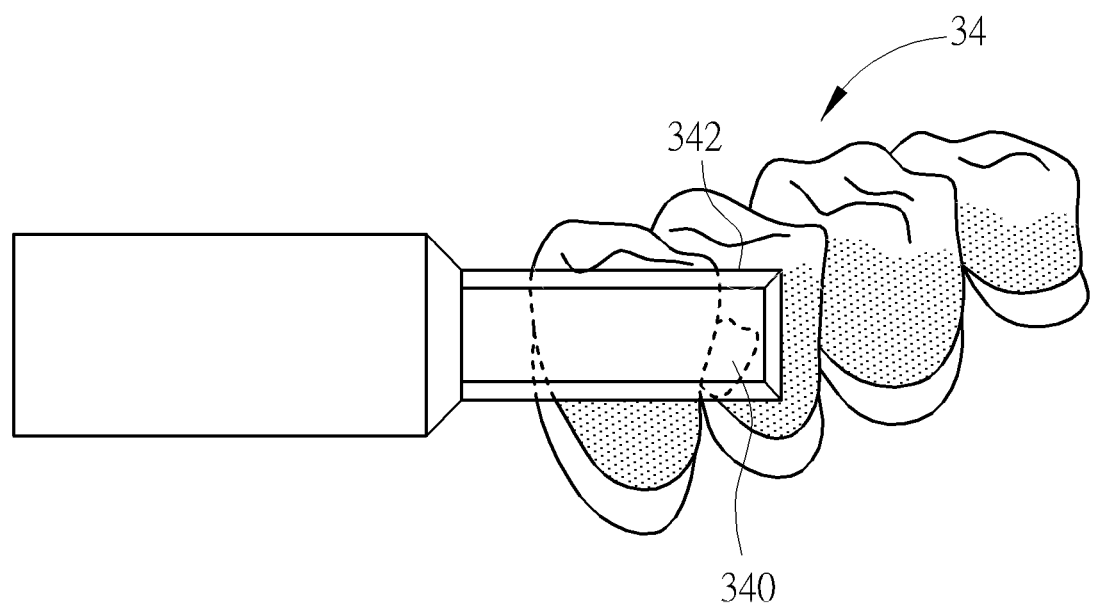
FIG. 5 is a schematic diagram illustrating an indication mark displayed at the incomplete area of the model.

Referring to FIG. 5, FIG. 5 is a schematic diagram illustrating an indication mark 342 displayed at the incomplete area 340 of the model 34. After positioning the incomplete area 340 in the model 34, the processing unit 16 may display an indication mark 342 (e.g. a pattern of intraoral scanner) at the incomplete area, so as to indicate where the incomplete area 340 is located in the model 34 for the user. Accordingly, the user can operate the intraoral scanner to scan and re-model the incomplete area 340 immediately. It should be noted that the indication mark 342 may be other patterns according to practical applications, so the indication mark 342 is not limited to the pattern of intraoral scanner. Furthermore, the invention may display the model 34 and the indication mark 342 by a display unit (e.g. liquid crystal display device, organic light emitting diode display device or other display devices, not shown) coupled to the processing unit 16, wherein the display unit may be disposed in the intraoral scanner or the host device according to practical applications.

Figure 6:
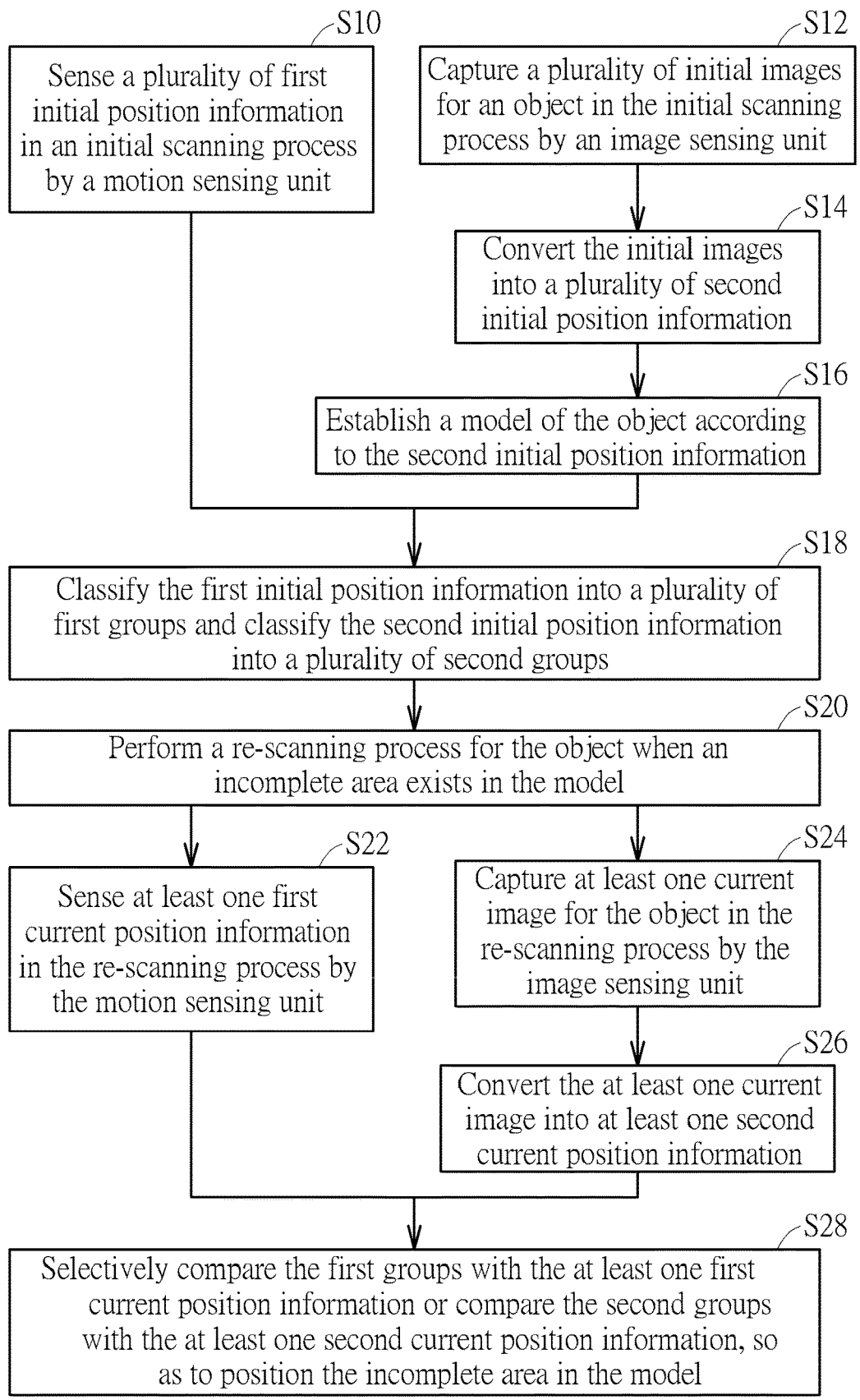
FIG. 6 is a flowchart illustrating an intraoral scanning method according to an embodiment of the invention.

Referring to FIG. 6, FIG. 6 is a flowchart illustrating an intraoral scanning method according to an embodiment of the invention. The intraoral scanning method shown in FIG. 6 can be implemented by the aforesaid intraoral scanning system 1. First, step S10 is performed to sense a plurality of first initial position information in an initial scanning process by a motion sensing unit 10. At the same time, step S12 is performed to capture a plurality of initial images for an object 32 in the initial scanning process by an image sensing unit 12. Then, step S14 is performed to convert the initial images into a plurality of second initial position information. Then, step S16 is performed to establish a model 34 of the object 32 according to the second initial position information. Then, step S18 is performed to classify the first initial position information into a plurality of first groups and classify the second initial position information into a plurality of second groups. Then, step S20 is performed to perform a re-scanning process for the object 32 when an incomplete area 340 exists in the model 34. Then, step S22 is performed to sense at least one first current position information in the re-scanning process by the motion sensing unit 10. At the same time, step S24 is performed to capture at least one current image for the object 32 in the re-scanning process by the image sensing unit 12. Then, step S26 is performed to convert the at least one current image into at least one second current position information. Then, step S28 is performed to selectively compare the first groups with the at least one first current position information or compare the second groups with the at least one second current position information, so as to position the incomplete area 340 in the model 34.

It should be noted that the detailed embodiments of the intraoral scanning method of the invention are mentioned in the above and those will not be depicted herein again. Furthermore, each part or function of the control logic of the intraoral scanning method shown in FIG. 6 may be implemented by software, hardware or the combination thereof.

As mentioned in the above, the invention classifies the first position information and the second position information obtained by the motion sensing unit and the image sensing unit in the initial scanning process into first groups and second groups. Then, the invention selectively uses the first groups or the second groups to perform comparison in the re-scanning process, so as to position the incomplete area in the model. Since the invention need not compare all position information obtained in the re-scanning process with the model established previously one by one, the invention can reduce the amount of data for comparison in the re-scanning process effectively, so as to save computation resources and time.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An intraoral scanning system comprising:
    a motion sensing unit sensing a plurality of first initial position information in an initial scanning process of the intraoral scanning system;
    an image sensing unit capturing a plurality of initial images for an object in the initial scanning process;
    a storage unit; and
    a processing unit coupled to the motion sensing unit, the image sensing unit and the storage unit, the processing unit converting the initial images into a plurality of second initial position information and storing the first position information and the second initial position information in the storage unit, the processing unit establishing a model of the object according to the second initial position information, classifying the first initial position information into a plurality of first groups, and classifying the second initial position information into a plurality of second groups;
    wherein when an incomplete area exists in the model, the intraoral scanning system performs a re-scanning process for the object; the motion sensing unit senses at least one first current position information in the re-scanning process, the image sensing unit captures at least one current image for the object in the re-scanning process, the processing unit converts the at least one current image into at least one second current position information, the processing unit selectively compares the first groups with the at least one first current position information or compares the second groups with the at least one second current position information, so as to position the incomplete area in the model.

2. The intraoral scanning system of claim 1, wherein the processing unit selectively compares the first groups with the at least one first current position information or compares the second groups with the at least one second current position information according to an image quality of the current image.

3. The intraoral scanning system of claim 2, wherein the image quality is represented by contrast ratio, acutance or amount of data points.

4. The intraoral scanning system of claim 1, wherein the first initial position information and the second initial position information are represented by angle information, the processing unit classifies the first initial position information into the first groups and classifies the second initial position information into the second groups according to a predetermined angle range.

5. The intraoral scanning system of claim 1, wherein when the processing unit compares the first groups with the at least one first current position information, the processing unit selects a target first group, which is more approximate to the at least one first current position information, from the first groups and compares the target first group with the at least one first current position information, so as to position the incomplete area in the model.

6. The intraoral scanning system of claim 1, wherein when the processing unit compares the second groups with the at least one second current position information, the processing unit selects a target second group, which is more approximate to the at least one second current position information, from the second groups and compares the target second group with the at least one second current position information, so as to position the incomplete area in the model.

7. The intraoral scanning system of claim 1, wherein after positioning the incomplete area in the model, the processing unit displays an indication mark at the incomplete area.

8. An intraoral scanning method comprising steps of:
    sensing a plurality of first initial position information in an initial scanning process by a motion sensing unit;
    capturing a plurality of initial images for an object in the initial scanning process by an image sensing unit;
    converting the initial images into a plurality of second initial position information;
    establishing a model of the object according to the second initial position information;

classifying the first initial position information into a plurality of first groups and classifying the second initial position information into a plurality of second groups;

when an incomplete area exists in the model, performing a re-scanning process for the object;

sensing at least one first current position information in the re-scanning process by the motion sensing unit;

capturing at least one current image for the object in the re-scanning process by the image sensing unit;

converting the at least one current image into at least one second current position information; and selectively comparing the first groups with the at least one first current position information or comparing the second groups with the at least one second current position information, so as to position the incomplete area in the model.

9. The intraoral scanning method of claim 8, wherein the intraoral scanning method selectively compares the first groups with the at least one first current position information or compares the second groups with the at least one second current position information according to an image quality of the current image.

10. The intraoral scanning method of claim 9, wherein the image quality is represented by contrast ratio, acutance or amount of data points.

11. The intraoral scanning method of claim 8, wherein the first initial position information and the second initial position information are represented by angle information, the intraoral scanning method classifies the first initial position information into the first groups and classifies the second initial position information into the second groups according to a predetermined angle range.

12. The intraoral scanning method of claim 8, wherein when comparing the first groups with the at least one first current position information, the intraoral scanning method further comprises steps of:

selecting a target first group, which is more approximate to the at least one first current position information, from the first groups; and comparing the target first group with the at least one first current position information, so as to position the incomplete area in the model.

13. The intraoral scanning method of claim 8, wherein when comparing the second groups with the at least one second current position information, the intraoral scanning method further comprises steps of:

selecting a target second group, which is more approximate to the at least one second current position information, from the second groups; and comparing the target second group with the at least one second current position information, so as to position the incomplete area in the model.

14. The intraoral scanning method of claim 8, wherein after positioning the incomplete area in the model, the intraoral scanning method further comprises step of:

displaying an indication mark at the incomplete area.

\* \* \* \* \*